United States Patent [19]

Schneider et al.

[11] 4,203,901

[45] May 20, 1980

[54] PROCESS FOR MAKING N-(N'-METHYLENEPYRROLIDONYL)-2-SUBSTITUTED ANILINES

[75] Inventors: Louis Schneider, Elizabeth; David E. Graham, Westfield, both of N.J.

[73] Assignee: GAF Corporation, New York, N.Y.

[21] Appl. No.: 962,305

[22] Filed: Nov. 20, 1978

Related U.S. Application Data

[63] Continuation-in-part of Ser. No. 892,146, Mar. 31, 1978, Ser. No. 928,569, Jul. 29, 1978, Ser. No. 935,354, Aug. 21, 1978, Ser. No. 942,644, Sep. 15, 1978, and Ser. No. 955,483, Oct. 26, 1978.

[51] Int. Cl.² ............................................ C07D 207/44
[52] U.S. Cl. ...................... 260/326.5 S; 260/326.5 FL
[58] Field of Search ............... 260/326.5 FL, 326.5 S; 544/165; 546/243

[56] References Cited

U.S. PATENT DOCUMENTS 3,136,766   6/1964   Buc et al. .............................. 546/243
3,950,393   4/1976   Keck et al. ........................... 544/165

Primary Examiner—Jose Tovar
Attorney, Agent, or Firm—Walter C. Kehm; Walter Katz

[57] ABSTRACT

This invention relates to a process for making N-(N'-methylenepyrrolidonyl)-2-substituted anilines in high yield. The products are useful intermediates in the synthesis of herbicides.

The process comprises reacting substantially equivalent molar concentrations of a 2-substituted aniline, as defined herein, with N-methylolpyrrolidone in an aromatic hydrocarbon solvent in the absence of an acid or base catalyst at a reflux temperature of 80°–140° C. while simultaneously and continuously distilling out from the reaction mixture an azeotrope consisting essentially of water and solvent until substantially all the water produced during the reaction has been removed thereby, and, thereafter, crystallizing the product from the remaining solution.

3 Claims, No Drawings

PROCESS FOR MAKING N-(N'-METHYLENEPYRROLIDONYL)-2-SUBSTITUTED ANILINES

This application is a continuation-in-part of Ser. Nos. 892,146 filed Mar. 31, 1978 now pending; 928,569 filed July 29, 1978 now pending; 935,354 filed Aug. 21, 1978 now pending; 942,644 filed Sept. 15, 1978 now pending; and 955,483, filed Oct. 26, 1978, now pending.

BACKGROUND OF THE INVENTION

1. Field of the Invention

This invention relates to a process of making N-(N'-methylenepyrrolidonyl)-2-substituted anilines which are intermediates in making useful herbicides.

2. Description of the Prior Art

U.S. Pat. Nos. 3,769,301 and 3,907,544 disclose related herbicidal compounds; however, these compounds are made by a different process. Accordingly, it is an object of this invention to provide a new and improved process for making intermediates in the synthesis of herbicidally active compounds.

U.S. Pat. Nos. 3,853,910 and 3,956,313 describes a condensation reaction of N-methyolpyrrolidone with alcohols and thioalcohols, respectively in the presence of an acid catalyst. U.S. Pat. No. 4,105,671 uses a basic catalyst in a similar reaction.

SUMMARY OF THE INVENTION

This invention relates to a process for making N-(N'-methylenepyrrolidonyl)-2-substituted aniline intermediate compounds in high yield having the formula:

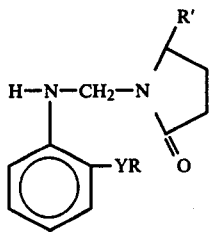

where
R is
  alkyl, $C_1$–$C_6$,
  alkenyl, $C_3$–$C_5$,
  alkyleneoxyalkyl, —$(CH_2)_n$ OR" where n=1–3, and R" is alkyl, $C_1$–$C_3$,
  cycloalkyl,

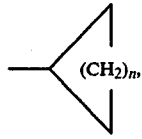

where n'=0–3,
R' is hydrogen or alkyl, $C_1$–$C_3$, and
Y is oxygen or sulfur.

DETAILED DESCRIPTION OF THE INVENTION

The starting material in the process of this invention is a 2-substituted aniline which is usually commercially available; otherwise it is made from 2-nitrophenol or 2-nitrothiophenol by reaction with a halogenated alkyl ether, a cycloalkyl halide, an alkyl halide or alkenyl halide to form the 2-substituted oxynitrobenzene or an 2-substituted thionitrobenzene. The nitro group then is reduced to the corresponding aniline.

The essential step in the overall process, which is the subject of this invention, is the reaction of the thus prepared aniline with N-methylolpyrrolidone to form the desired N-(N'-methylene-pyrrolidonyl)-2-substituted aniline. This step is carried out advantageously, as a feature of the invention, to provide the intermediate aniline in high yield by heating a reaction mixture containing substantially equivalent molar amounts of the reactants in a solvent under non-catalyzed conditions at a reflux temperature of about 80°–140° C. while simultaneously and continuously distilling out an azeotrope consisting essentially of water and solvent until substantially a stoichiometric amount of water produced during the reaction has been removed thereby. The desired intermediate compound then is crystallized from the remaining solution.

In the preferred embodiment of the invention, the reaction is carried out in very high yield in the absence of any acid or base catalyst in an aromatic hydrocarbon solvent such as toluene or xylene.

The intermediate compounds produced by the process of the invention are acylated with a haloacetyl halide to form N-(haloacetyl) compounds which are useful herbicides.

As used herein, the term "alkyl" includes both straight and branched chain hydrocarbon radicals; and the term "alkenyl" includes straight, branched chain and cyclic hydrocarbons.

PREPARATION OF N-METHYLOLPYRROLIDONE

2-Pyrrolidone (212.4 g., 2.0 mole) and potassium hydroxide (0.6 g) are heated to 80° C. and paraformaldehyde (75.6 g, 2.6 mole) was added during 10 minutes, and the mixture was maintained at 75°–80° C. for ½ hour. The desired product then was crystallized from 1 part of benzene to yield 227 g. (88.2%), m.p. 78°–80° C. of product.

EXAMPLE 1

N-(N'-Methylene-2-Pyrrolidonyl)-2-Methoxyaniline

2-Methoxyaniline (24.6 g., 0.2 mole), xylene (100 cc) and N-methylolpyrrolidone (23.0 g., 0.2 mole) were refluxed while an azeotrope containing a stoichiometric amount of water was removed. The product then was crystallized from xylene-ehter, and vacuum dried, to yield 172 g. (89%), m.p. 106°–108° C. of product.

EXAMPLE 2

N-(N'-Methylene-2-Pyrrolidonyl)-2-sec-Butoxyaniline

A mixture of o-sec-butoxyaniline (32 g., 0.19 mole), N-methylol-2-pyrrolidone (21.9 g., 0.19 mole), and xylene (100 ml) were refluxed under azeotropic conditions for about 1¾ hours and about 2 ml. of water was collected. The xylene solution was washed with 5% hydrochloric acid followed by three water washes. The xylene layer was dried over magnesium sulfate and the solvent removed by rotoevaporation yielding 46.5 g. (97.8%) of product.

EXAMPLE 3

N-(N'-Methylene-5-Methyl-2-Pyrrolidonyl)-2-Ethoxyaniline

A mixture of N-hydroxymethyl-5-methyl-2-pyrrolidone (25.8 g., 0.20 moles), o-ethoxyaniline (27.5 g., 0.20 moles), and xylene (81 ml.) were refluxed for 1 hour while removing water; then an additional 25 ml. of xylene was added and refluxing continued for 3 hours. The xylene was removed by rotoevaporation and the residue crystallized on standing. Recrystallized from methanol provided 25.9 g. of product (52.1% yield) m.p. 89°–91° C.

EXAMPLE 4

N-(N'-Methylene-2-Pyrrolidonyl)-2-Cyclopentoxyaniline

A. 2-Cyclopentoxynitrobenzene

2-Nitrophenol (83.5 g, 0.60 mole), cyclopentyl bromide (98.0 g, 0.66 mole), anhydrous potassium carbonate (82.9 g, 0.60 mole) and dry acetone (600 cc) were refluxed for 72 hours, and filtered to remove the potassium bromide. The residue was washed with acetone and the solvent was removed by rotary evaporation. The residue was partitioned between 200 cc of dichloromethane and water. The dichloromethane layer was washed with 200 cc of 10% potassium hydroxide, separated and the solvent was removed by rotary evaporation. The crude product was fractionally distilled at 144°–146° C. at 1.0 mm. Hg to yield 58.2 g of product (46.8%).

B. 2-Cyclopentoxyaniline

Iron 60 mesh (51.9 g, 0.93 mole), water (220 cc), ethanol (244 cc) and concentrated hydrochloric acid (14.2 cc) were heated to reflux under a nitrogen blanket. Then 2-cyclopentoxynitrobenzene (55.2 g, 0.27 mole) was added at reflux over a period of 2 hours. The reaction was maintained at reflux for an additional 3 hours. The pH was adjusted to 7–8 by the addition of concentrated ammonium hydroxide. The reaction mixture then was filtered at 30° C., and the filtrate was washed with 200 cc of ether. The filtrate was extracted with 4×50 cc of ether and the combined ether extracts were subjected to rotary evaporation. The crude product was fractionally distilled at 126°–130° C. at 2.0–2.5 mm. Hg to yield 30.3 g (64.3%) of product.

C.

2-Cyclopentoxyaniline (10.0 g, 0.057 mole), N-methylol-2-pyrrolidone (9.75 g, 0.85 mole) and xylene (25 cc) were refluxed under azeotropic conditions with the removal of 1.5 cc of water. The xylene was removed by rotary evaporation and the product was crystallized from 100 cc of hexane to yield 8.0 g (51.6%) of product, m.p. 87°–87.5° C.

EXAMPLE 5

N-(N'-Methylene-5-Methyl-2-Pyrrolidonyl)-2-Methylmercaptoaniline

2-Methylmercaptoaniline, N-hydroxymethyl-5-methyl-2-pyrrolidone and toluene were reacted in a similar manner as described in Example 1.

EXAMPLE 6

N-(N'-Methylenepyrrolidonyl)-2-Isopropylmercaptoaniline

A. 2-Isopropylmercaptoaniline

2-Nitrothiophenol, 2-bromopropane, potassium carbonate and acetone were refluxed for several hours. The solvent then was removed by rotary evaporation. The crude product was partitioned between methylene chloride and a 10% sodium carbonate solution. The organic phase was distilled to yield 2-isopropylmercaptonitrobenzene.

B.

This intermediate was reduced to the corresponding aniline by reduction with iron, concentrated hydrochloric acid and ethanol. The mercaptoaniline was isolated by vacuum distillation.

C.

2-Isopropylmercaptoaniline and N-methylolpyrrolidone were condensed in toluene with the removal of water as described in Example 1.

EXAMPLE 7

N-(N'-Methylene-2-Pyrrolidonyl)-2-Butylmercaptoaniline

2-Butylmercaptoaniline was prepared from -2-nitrothiophenol by a two-step reaction sequence consisting of alkylation followed by reduction corresponding to the procedure described in Example 4. The aniline then was condensed with N-methylol-2-pyrrolidone to yield the desired product.

EXAMPLE 8

N-(N'-Methylene-2-Pyrrolidonyl-2-Propen-2-yl-mercaptoaniline

2-Propen-2-yl-mercaptoaniline was prepared by reduction of 2-propen-2-yl-mercaptonitrobenzene, which was obtained by condensing 2-nitrothiophenol and allylbromide, to give the corresponding aniline.

Then 2-propen-2-yl-mercaptoaniline and N-methylol-2-pyrrolidone were condensed in toluene with the removal of water to form the desired product.

EXAMPLE 9

N-(N'-Methylene-2-Pyrrolidonyl)-2-Ethoxyethylmercaptoaniline

2-Ethoxyethylmercaptoaniline was prepared by reduction of 2-ethoxyethylmercaptonitrobenzene, which was obtained by condensation of 2-nitrothiophenol and 2-bromoethyl ethyl ether, to give the corresponding aniline. The 2-ethoxyethylmercaptoaniline and N-methylol-2-pyrrolidone were then condensed in toluene with the removal of water to form the methylenepyrrolidonylaniline in high yield.

EXAMPLE 10

N-(N'-Methylene-2-Pyrrolidonyl)-2-Cyclopentylmercaptoaniline

2-Cyclopentylmercaptoaniline was prepared by reduction of 2-cyclopentylmercaptonitrobenzene, which was obtained from 2-nitrothiophenol and bromocyclopentane followed by reduction to the corresponding aniline. The 2-cyclopentylmercaptoaniline was subsequently condensed in toluene with the removal of water to form the desired product in high yield.

EXAMPLE 11

N-(N'-Methylene-2-Pyrrolidonyl)-2-Methylmercaptoaniline

2-Methylmercaptoaniline (50.0 g, 0.36 mole), N-methylol-2-pyrrolidone (41.3 g, 0.36 mole) and toluene (145 cc) were refluxed under azeotropic conditions until the stoichiometric amount of water was removed. The reaction was washed successively with 100 cc of 10% hydrochloric acid, 100 cc of 10% sodium carbonate and finally with water. The toluene phase was dried over magnesium sulfate and removed by rotary evaporation. The product (69 g, 81.5% yield) was isolated as an oil.

EXAMPLE 12

N-(N'-Methylene-2-Pyrrolidonyl)-2-Ethylmercaptoaniline

2-Ethylmercaptoaniline, N-methylol-2-pyrrolidone and toluene were condensed with the removal of water to form the desired product.

EXAMPLE 13

N-(N'-Methylene-2-Pyrrolidonyl)-2-Ethoxyethoxyaniline

A. 2-Ethoxyethoxynitrobenzene

2-Nitrophenol (91.0 g., 0.65 mole), 2-bromoethyl ethyl ether (100.0 g., 0.65 mole), anhydrous potassium carbonate (9.0 g, 0.72 mole) and acetone (1 liter) were refluxed for 65 hours. The reaction mixture was filtered, and the acetone removed by rotary evaporation. The residue was partitioned between 200 ml. of dichloromethane and 100 ml water. The organic phase was further washed with 200 ml. of 10% sodium hydroxide followed by 100 cc of water. The product (58.0 g) was obtained in 42% yield by a vacuum distillation (100°–120° C./0.5 mm).

B. 2-Ethoxyethoxyaniline

Iron 60 mesh (54.0 g, 0.96 mole), concentrated hydrochloric acid (15 cc), ethanol (260 cc) and water (230 cc) were heated to reflux under a nitrogen blanket; 2-ethoxyethoxynitrobenzene (58.0 g, 0.28 mole) was added at reflux over 4 hours, and reflux continued for an additional 3 hours. The reaction mixture then was neutralized with concentrated ammonium hydroxide to a pH of 8–9, and filtered through a Celite bed. The iron cake was washed with 200 cc of ether, and the organic phase was separated. The product (20.0 g) was obtained in 40.2% yield by a vacuum distillation (111°–135° C./2–4 mm.)

C.

2-Ethoxyethoxyaniline (20.0 g, 0.11 mole), N-methylol-2-pyrrolidone (13.5 g., 0.11 mole) and 100 cc xylene were refluxed under azeotropic conditions until the stoichiometric amount of water was removed (1.0 cc). The xylene layer then was washed with 2×50 cc of water, dried over magnesium sulfate and filtered. The xylene was removed by rotary evaporation. The crude product was solubilized in dichloromethane, and purified by column chromotography, using a 2.4:5.6:2.0 chloroform:hexane:acetone solvent system to yield 16.2 g of product; 53% yield.

EXAMPLE 14

N-(N'-Methylene-2-Pyrrolidonyl)-2-Propoxymethoxyaniline

2-Nitrophenol, bromomethyl propyl ether, anhydrous potassium carbonate and acetone were reacted according to the procedure outlined in Example 1 to yield 2-propoxymethoxynitrobenzene, which was reduced to the corresponding aniline, and isolated by a vacuum distillation.

2-Propoxymethoxyaniline, N-methylol-2-pyrrolidone and xylene then were condensed while removing water to form the product.

EXAMPLE 15

N-(N'-Methylene-2-Pyrrolidonyl)-2-Methoxypropoxyaniline

2-Nitrophenol, 3-bromopropyl methyl ether, anhydrous potassium carbonate and acetone were reacted according to the procedure outlined in Example 1 to yield 2-methoxypropoxynitrobenzene, which was reduced to the corresponding aniline. The aniline was isolated by vacuum distillation.

2-Methoxypropoxyaniline, N-methylol-2-pyrrolidone and xylene then were condensed while removing water to form the desired product.

EXAMPLE 16

N-(N'-Methylene-2-Pyrrolidonyl)-2-Prop-1-en-oxyaniline

A. 2-Prop-1-en-oxynitrobenzene

2-Nitropehnol (142.0 g, 1.02 mole), allyl bromide (120.9 g, 1.00 mole), anhydrous potassium carbonate (140.0 g, 1.02' mole) and dry acetone (500 cc) were refluxed for 21 hours, and filtered to remove the potassium bromide. The residue was washed with acetone and the solvent was removed by rotary evaporation. The residue was partitioned between 200 cc of dichloromethane and water. The dichloromethane layer was washed with 200 cc of 10% potassium hydroxide, separated and the solvent was removed by rotary evaporation. The crude product was fractionally distilled at 124° C. at 2.0 mm. Hg to yield 164.7 g of product (91.9%).

B. 2-Prop-1-en-oxyaniline

Iron 60 mesh (106.3 g, 1.9 mole), water (450 cc), ethanol (500 cc) and concentrated hydrochloric acid (29.5 cc) were heated to reflux under a nitrogen blanket. Then 2-prop-1-en-oxynitrobenzene (89.6 g, 0.57 mole) was added at reflux over a period of 2 hours. The reaction was maintained at reflux over a period of 2 hours. The reaction was maintained at reflux for an additional 3 hours. The pH was adjusted to 7–8 by the addition of concentrated ammonium hydroxide. The reaction mixture then was filtered at 30° C., and the filtrate was washed with 200 cc of ether. The filtrate was extracted with 4×50 cc of ether and the combined ether extracts were subjected to rotary evaporation. The crude product was fractionally distilled at 110°–112° C. at 4.5 mm. Hg to yield 50.1 g (67.2%) of product.

C.

2-Prop-1-en-oxyaniline (5.6 g, 0.037 mole), N-methylol-2-pyrrolidone (5.0 g, 0.037 mole) and toluene (25 cc) were refluxed under azeotropic conditions with the removal of 0.7 cc of water. The toluene was removed by rotary evaporation and the product was crystallized from 50 cc of ether to yield the desired product, m.p. 79°–80° C.

EXAMPLE 17

N-(N'-Methylene-2-Pyrrolidonyl)-2-But-1-en-oxyaniline

4-Bromobutene-1 was reacted with o-nitrophenol to yield 2-but-1-en-oxynitrobenzene; which was reduced to the corresponding aniline; and reacted with N-methylol-2-pyrrolidone to form the corresponding N-methylenepyrrolidonyl derivative.

EXAMPLE 18

N-(N'-Methylene-2-Pyrrolidonyl(2-Methylprop-1-en-oxy)aniline

3-Chloro-2-methyl propene-1 was reacted with o-nitrophenol to yield 2-(2-methyl prop-1-en-oxy)nitrobenzene; which was reduced to the corresponding aniline; reacted with N-methylol-2-pyrrolidone to form the corresponding N-methylenepyrrolidonyl derivative.

EXAMPLE 19

N-(N'-Methylene-2-Pyrrolidonyl)-2-But-2-en-oxyaniline

2-Bromo-but-2-ene was reacted with o-nitrophenol to yield 2-but-1-en-oxynitrobenzene; which was reduced to the corresponding aniline; then reacted with N-methylol-2-pyrrolidone to form the corresponding N-methylene-2-pyrrolidonyl derivative.

EXAMPLE 20

N-(N'-Methylene-5-Methyl-2-pyrrolidonyl)-2-Prop-1-en-oxyaniline

Allyl bromide was reacted with o-nitrophenol to yield 2-prop-1-en-oxynitrobenzene; which was reduced to the corresponding aniline; then reacted with N-hydromethyl-5-methyl-2-pyrrolidone to form the corresponding N-5-methyl-N-methylene-2-pyrrolidonyl derivative.

EXAMPLE 21

N-(N'-Methylene-5-methyl-2-pyrrolidonyl)-2-Cyclopent-3-en-oxyaniline

Cyclo-pent-3-en-1-ol was reacted with o-nitrophenol to yield 2-cyclopent-3-en-oxy nitrobenzene; which was reduced to the corresponding aniline; then reacted with N-hydromethyl-5-methyl-2-pyrrolidone to form the corresponding N-5-methyl-N-methylene-2-pyrrolidonyl derivative.

What we claim is:

1. A process for making intermediate compounds having the formula:

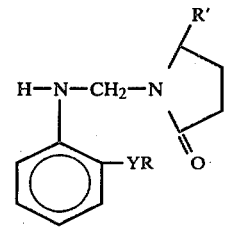

where
R is
 alkyl, $C_1$–$C_6$,
 alkenyl, $C_3$–$C_5$,
 —$(CH_2)_{n'}$OR" wherein n'=1–3, and R" is alkyl, $C_1$–$C_3$,

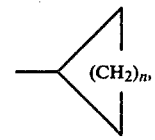

where n'=0–3,
R' is hydrogen or alkyl, $C_1$–$C_3$ and
Y is oxygen or sulfur,
which comprises:
 (a) heating a reaction mixture containing substantially equivalent molar amounts of a 2-substituted aniline having the formula:

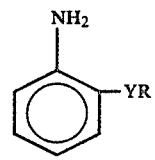

and an N-hydroxy methylenepyrrolidone having the formula:

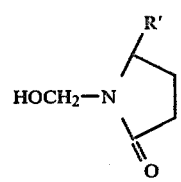

where R, R' and Y are as defined above, in a solvent, under non-catalyzed conditions, at a reflux temperature of about 80°–140° C.,
 (b) simultaneously and continuously distilling out from the reaction mixture an azeotrope consisting essentially of water and solvent until substantially all the water produced during the reaction has been removed thereby, and thereafter,
 (c) crystallizing the product from the remaining solution.

2. A process according to claim 1 wherein said solvent is an aromatic hydrocarbon.

3. A process according to claim 1 wherein said solvent is toluene or xylene.

* * * * *